US009220245B2

(12) United States Patent
Alves

(10) Patent No.: US 9,220,245 B2
(45) Date of Patent: Dec. 29, 2015

(54) METHODS OF USING FIELD-DERIVED COLONIES OF INSECTS SELECTED FOR DECREASED SUSCEPTIBILITY TO PLANTS EXPRESSING INSECTICIDAL TOXINS

(75) Inventor: Analiza Alves, Windsor Heights, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 155 days.

(21) Appl. No.: 13/315,351

(22) Filed: Dec. 9, 2011

(65) Prior Publication Data

US 2012/0148497 A1  Jun. 14, 2012

Related U.S. Application Data

(60) Provisional application No. 61/422,216, filed on Dec. 12, 2010.

(51) Int. Cl.
| | |
|---|---|
| *A61K 49/00* | (2006.01) |
| *A01K 67/033* | (2006.01) |
| *A01N 25/00* | (2006.01) |
| *C12N 15/82* | (2006.01) |

(52) U.S. Cl.
CPC ............ *A01K 67/033* (2013.01); *A01N 25/006* (2013.01); *C12N 15/8286* (2013.01)

(58) Field of Classification Search
CPC . A01K 67/033; A01N 20/00; C12N 15/8286; G01N 33/5085
See application file for complete search history.

(56) References Cited

FOREIGN PATENT DOCUMENTS

WO   WO 2009/132850   * 11/2009 ............. C12N 15/82

OTHER PUBLICATIONS

M. Willrich Siebert et al., Efficacy of CRY1F Insecticidal Protein in Maize and Cotton for Control of Fall Armyworm (Lepidoptera: Noctuidae).Florida Entomol, 2008, 91:555-565.*
Adamczyk et al., Larval Survival and Development of the Fall Armyworm (Lepidoptera: Noctuidae) on Normal and Transgenic Cotton Expressing the Bacillus thuringiensis CrylA (c) a-endotoxin. Journal of Economic Entomology. 1998, vol. 91, No. 2: 539-545.*
Farias et al., Field-evolved resistance to Cry1F maize by Spodoptera frugiperda (Lepidoptera: Noctuidae) in Brazil. Crop Protection 64 (2014) 150-158.*
Storer, et al., "Discovery and Characterization of Field Resistance to Bt Maize: Spodoptera frugiperdia (Lepidoptera: Noctuidae) in Puerto Rico", Journal of Ecomonic Entomology; vol. 103(4):1031-1038 (2010).
Liu, et al., "Resistance Allele Frequency to Bt Cotton in Field Populations of Helicoverpa armigera (Lepidoptera: Noctuidae) in China", Journal of Economic Entomology; vol. 101(3): 933-943 (2008).
Gould, et al., "Initial frequency of alleles for resistance to Bacillus thuringiensis toxins in field populations of Heliothis virescens", Proceedings of the National Academy of Sciences; vol. 94(8): 3519-3523 (1997).
Liu, et al., "Evidence of field-evolved resistance to Cry1Ac-expressing Bt cotton in Helicoverpa armigera (Lepidoptera: Noctuidae) in northern China", Pest Management Science; vol. 66(2): 155-161 (2009).
Xu, et al., "Using an F 2 screen to monitor frequency of resistance alleles to Bt cotton in field populations of Helicoverpa armigera (Hubner) (Lepidoptera: Noctuidae)", Pest Management Science; vol. 65(4): 391-397 (2009).
Adamczyk, J.J., et al., "Increased Tolerance of Fall Armyworms (Leopidoptera: Noctuidae) to Cry1Ac d-Endotoxin when Fed Transgenic Bacillus thuringiensis Cotton: Impact on the Development of Subsequent Generations", Florida Entomologist; vol. 84(1): 1-6; 2001.
Hernandez, C., et al., "Common Receptor for Bacillus thuringiensis Toxins Cry1Ac, Cry1Fa, and Cry1Ja in Helicoverpa armigera, Helicoverpa zea, and Spodoptera exigua", Applied and Environmental Microbiology; vol. 71(9): 5627-5629; 2005.
Siebert, M., et al., "Evaluation of Corn Hybrids Expressing Cry1F (Herculex I Insect Protection) Against Fall Armyworm (Lepidoptera: Noctuidae) in the Southern United States", J. Entomol. Sci.; vol. 43(1) 41-51; 2008.

* cited by examiner

*Primary Examiner* — Scott Long
*Assistant Examiner* — Arthur S Leonard
(74) *Attorney, Agent, or Firm* — Pioneer Hi-Bred Int'l, Inc.

(57) ABSTRACT

Methods are provided for using field-derived colonies of insects that comprise field-evolved resistance to insecticidal toxins that are produced in transgenic plants. The methods find use in resistance management strategies for transgenic crop plants expressing insecticidal toxins.

6 Claims, 2 Drawing Sheets

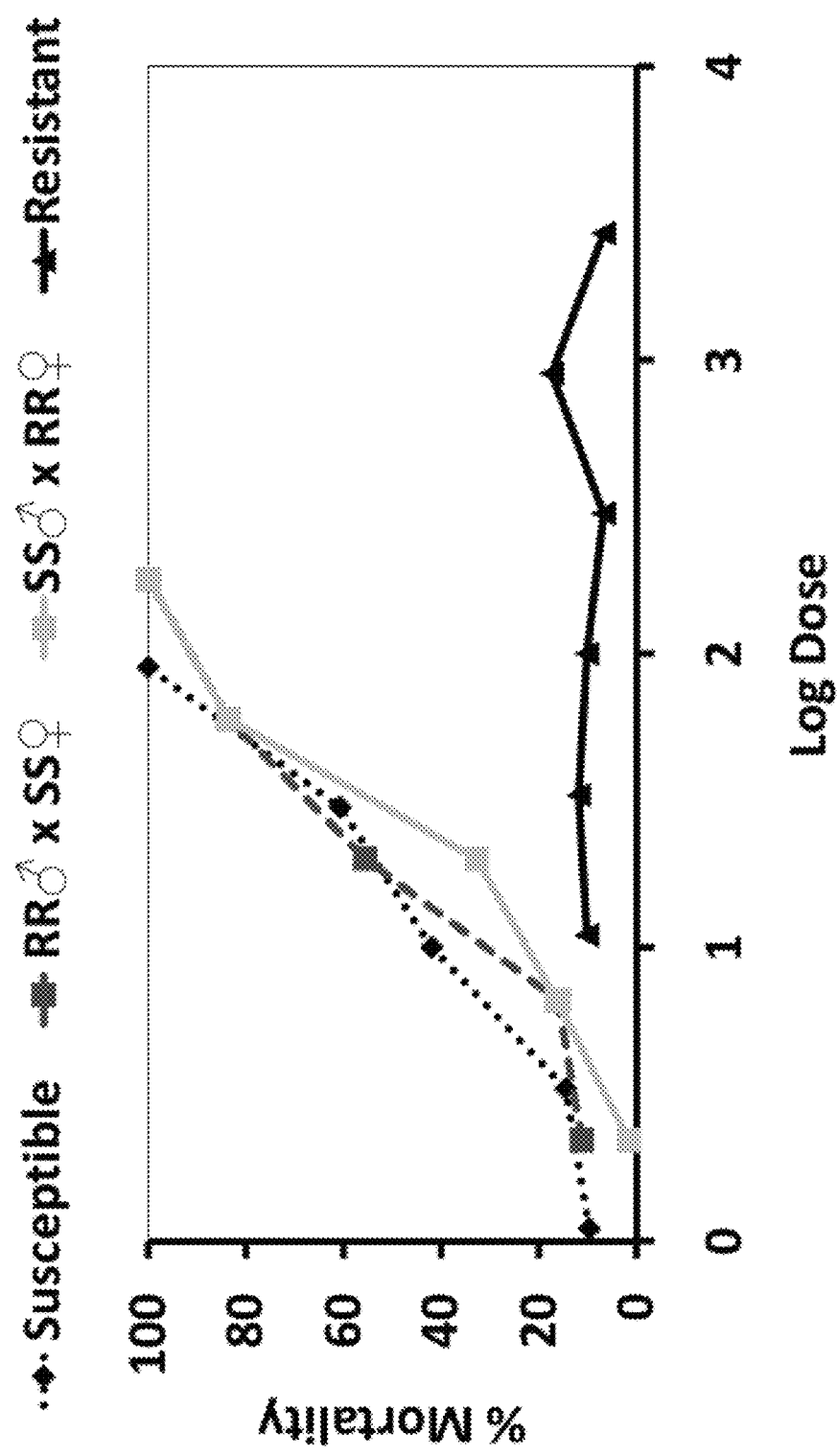

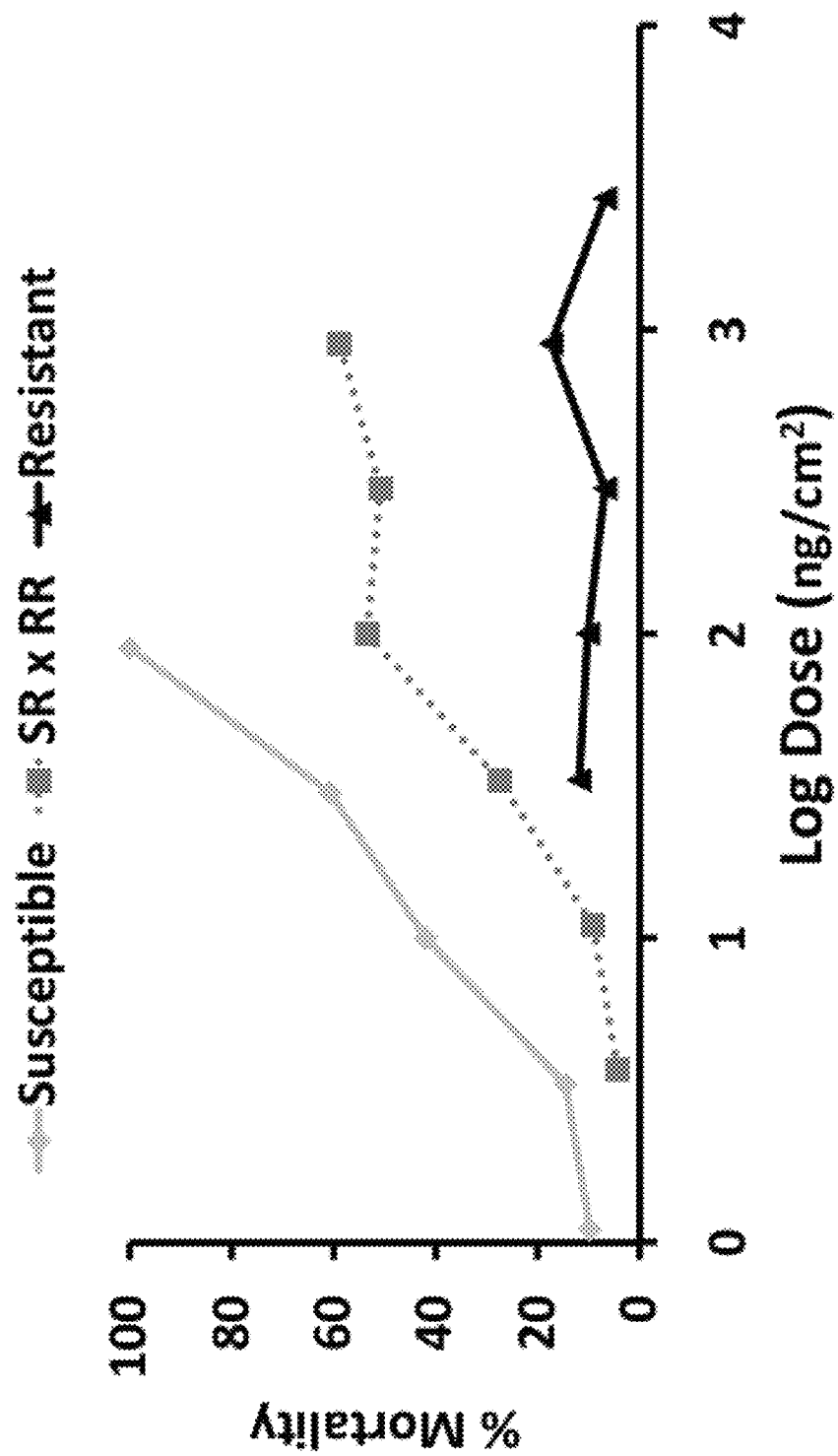

METHODS OF USING FIELD-DERIVED COLONIES OF INSECTS SELECTED FOR DECREASED SUSCEPTIBILITY TO PLANTS EXPRESSING INSECTICIDAL TOXINS

CROSS REFERENCE TO RELATED APPLICATIONS

This application claims priority under 35 U.S.C. §119(e) to provisional application Ser. No. 61/422,216 filed Dec. 12, 2010, herein incorporated by reference in its entirety.

FIELD OF THE INVENTION

The present invention relates to methods of using field-derived colonies of insects with increased tolerance to transgenic crop plants expressing insecticidal toxins.

BACKGROUND OF THE INVENTION

Corn, *Zea mays* L., is one of the crops most widely grown in the United States, with over 60 million acres of corn planted annually (Andow and Hutchison (1998) "Bt-corn resistance management". In *Now or never: serious new plans to save a natural pest control*, eds. Mellon and Rissler, eds., pp. 19-66, Union of Concerned Scientists, Cambridge, Mass.). Fall armyworm (FAW, *Spodoptera frugiperda* (J. E. Smith)) is one of the most important lepidopteran pests of corn in southern United States (Buntin (2008) *Florida Entomol.* 91:523-530), as well as Latin and South Americas. Damage by FAW involve leaf feeding, often observed in whorl stage plants, as well as ear feeding, causintg substantial yield losses. Insecticidal control to prevent ear damage in field corn is difficult and generally not cost effective. Transgenic corn expressing *Bacillus thuringiensis* (Bt) insecticidal toxins is an effective control technology against FAW offering great potential for reducing losses by this insect pest in field corn (Buntin et al. (2001) *Florida Entomol.* 84:37-42; Buntin et al. (2004) *J. Econ. Entomol.* 97:1603-1611). However, there is a concern that insects may rapidly develop resistance to the Bt expressed in plants in areas where continuous use and intensive selection pressure is applied (Mallet and Porter (1992) *Proc. R. Soc. B* 250:165-169; Chaufaux et al. (2001) *J. Econ. Entomol.* 94:1564-1570).

Insect resistance evolution has been well documented and is a serious problem in agricultural and livestock production, urban environments, and public health (Georghiou (1986) "The magnitude of resistance problem," In *Pesticide Resistance: strategies and tactics for management*, Council, ed., pp. 14-44, National Academy Press, Washington, D.C.; Roush and McKenzie (1987) *Annu. Rev. Entomol.* 32:361-380, Roush and Tabashnik (1990) *Pesticide resistance in arthropods*, New York, N.Y., Chapman and Hall). Bt is a valuable source of insecticidal proteins for use in insect pest control either in conventional spray formulations or in transgenic crops (Roush (1994) *Biocontrol Sci. Technol.* 4:501-516; Ferré and J. Van Rie (2002) *Annu. Rev. Entomol.* 47:501-533). Nonetheless, the evolution of insect resistance in field populations is an important threat to this technology (Ferré and J. Van Rie (2002) *Annu. Rev. Entomol.* 47:501-533), especially with transgenic plants that express Bt toxins (Mallet and Porter (1992) *Proc. R. Soc. B* 250:165-169).

Maize hybrids containing event TC1507 express both Cry1F and PAT genes. The Cry1F protein confers resistance to key Lepidopteran pests of maize, such as European corn borer (*Ostrinia nubilalis*), southwestern corn borer (*Diatraea grandiosella*), FAW, and black cutworm (*Agrotis ipsilon*). The pat gene encodes the PAT protein to confer tolerance to the herbicidal active ingredient glufosinate-ammonium. Maize hybrids containing event TC1507 have been widely adopted in the United States since its commercialization in 1998. As part of the regulatory submission a mandated insect resistance management (IRM) plan was proposed to delay the rate of evolution of resistance. Currently, the preferred and most widely adopted strategy involves the use of plants expressing a high dose of the Bt toxin in conjunction with planting a refuge of a non-Bt crop for preservation of susceptible genes (International Life Sciences Institute. Health and Environmental Sciences Institute (1999) *An evaluation of insect resistance management in Bt field corn: A science-based framework for risk assessment and risk management*; Tabashnik et al. 2003. *J. Econ. Entomol.* 96:1031-1038). This approach was considered to be most feasible and realistic in terms of farming practices and in prolonging the use of Bt transgenic crops (Gould (1998) *Annu. Rev. Entomol.* 43:701-726). However, there still is a concern that insects may develop resistance to the Bt expressed in plants in areas where continuous use and intensive selection pressure is applied (Mallet and Porter (1992) *Proc. R. Soc. B* 250:165-169; Chaufaux et al. (2001) *J. Econ. Entomol.* 94:1564-1570).

FAW populations in Puerto Rico have been exposed to microbial Bt formulation used in conventional insecticides, and to transgenic plants containing event TC1507 over several years, both containing Bt Cry1 insecticidal proteins. Even though the Cry1F toxin is uniquely efficacious in controlling FAW when compared to other Cry1 toxins (Waquil et al. (2002) *Revista Brasileira de Milho e Sorgo* 1:1-11; Waquil et al. (2004) *Revista Brasileira de Milho e Sorgo* 3:161-171), repeated exposures to this toxin and the unique conditions of Puerto Rico (i.e., tropical island geography, reduced availability of alternative hosts due to drought conditions, continuous corn growth, and high population density with overlapping generations) collaborated for increased pest population selection pressure and therefore increased likelihood for evolution of resistance.

BRIEF SUMMARY OF THE INVENTION

The present invention discloses the production of a field-derived colony of fall armyworm (FAW, *Spodoptera frugiperda*) selected for decreased susceptibility to maize plants expressing the insecticidal protein Cry1F. Thus, in one aspect the invention provides methods for producing a field-derived colony of FAW that comprises decreased susceptibility to maize plants producing Cry1F. FAW from such a field-derived colony comprise field-evolved resistance to Cry1F. The methods involve collecting FAW from a field comprising maize plants, particularly a field comprising maize plants that produce Cry1F, feeding the FAW leaf material from maize plants that express Cry1F, and selecting FAW individuals that survived exposure. The methods can further involve transfer of the surviving FAW to a standard fall armyworm diet that lacks Cry1F to allow the survivors to complete development. The methods can further involve allowing the surviving FAW to mate to maintain the colony with selection periodically applied in subsequent generations by feeding the FAW leaf material from maize plants that express Cry1F and selecting surviving FAW, and therefore fixing resistance by eliminating individuals that do not carry homozygous resistance alleles. It is recognized that the methods for producing a field-derived colony of FAW can be used in a like manner with other any other insect pest of that evolves resistance to one or more insecticidal toxins, particular one or more *Bacillus thuring-*

*iensis* (Bt) insecticidal toxins, that produced a transgenic plant, particularly a transgenic crop plant.

In one embodiment, the methods of the present invention were used to produce a field-derived colony of FAW (referred to herein as "FAW-SPR") with fixed alleles for resistance from eggs collected in Puerto Rico, USA in a field of transgenic maize plants comprising maize event TC1507, which express Cry1F. The FAW from this colony display decreased susceptibility to maize plants comprising maize event TC1507.

The present invention further provides methods for determining the frequency of resistance alleles in populations where resistance has not evolved. The methods involve collecting insects from a field or other site, mating virgin adults from the collected insects with virgin adult insects from a field-derived colony of the resistant insect of the same species as the collected insects, allowing larvae from the mating to feed on a diet comprising an insecticidal toxin at a concentration that is lethal to susceptible insects, and determining mortality. Such methods find use, for example, in the development of resistance management strategies.

In one embodiment of the invention, methods for determining the frequency of resistance alleles in populations of FAW where resistance to Cry1F has not evolved. The methods involve collecting FAW from a field or other site, mating virgin adults from the collected FAW with virgin adults from resistant FAW from the field-derived colony, allowing larvae from the mating to feed on a diet comprising Cry1F at a concentration that is lethal to susceptible FAW, and determining mortality. Such methods find use, for example, in the development of resistance management strategies.

The present invention further provides methods of using a field-derived colony of an insect pest of interest that comprises an insect pest of interest with field-evolved resistance to an insecticidal toxin that is expressed in a transgenic plant. Such a field-derived colony of an insect pest of interest can be produced, for example, by the methods disclosed herein or by any other method known in the art. The methods of the invention include, for example, using such a field-derived colony of an insect pest of interest in methods: for understanding the mechanism of the insect resistance to insecticidal toxin; for evaluating cross-resistance potential of the insecticidal toxin with any other existing or new insecticides or insecticidal proteins with activity against the insect pest of interest; to improve resistance monitoring strategies for the insect pest of interest in geographic locations where crop plants expressing the insecticidal toxin have been commercialized or are planned to be commercialized; of validating assumptions used in known resistance-risk computer simulation models for crop plants expressing the insecticidal toxin; for evaluating alternative refuge deployment strategies for crop plants, such as, for example, seed mixes or refuge-in-a-bag strategies; of investigating whether or not existing insect control tactics will affect the rate at which the insect pest of interest may develop resistance to transgenic crop plants expressing the insecticidal toxin under field conditions; to develop molecular marker technology to monitor for the development of resistance (change in resistant alleles' frequency) to the insecticidal toxin in field populations of the insect pest of interest; and to provide a better understanding on the mode of action of the insecticidal toxin in the control of the insect pest of interest.

In one embodiment of the invention, the insect pest is FAW and the insecticidal toxin is Cry1F expressed in transgenic maize plants, particularly transgenic maize plants comprising maize event TC1507. The methods of the invention include, for example, using such a field-derived colony of FAW in methods: for understanding the mechanism of fall armyworm resistance to Cry1F; for evaluating cross-resistance potential of Cry1F with any other existing or new insecticides or insecticidal proteins with activity against fall armyworm; to improve fall armyworm resistance monitoring strategies for TC1507 in maize in the continental U.S.A. and other geographic locations where event TC1507 maize has been commercialized or is planned to be commercialized; of validating assumptions used in known resistance-risk computer simulation models for maize event TC1507; for evaluating alternative refuge deployment strategies for event TC1507 maize, such as, for example, seed mixes or refuge-in-a-bag strategies; of investigating whether or not existing fall armyworm control tactics, namely MON810 and Bt11 maize plants, both of which express Cry1Ab, and chemical insecticides, will affect the rate at which fall armyworm may develop resistance to TC1507 under natural field conditions; to develop molecular marker technology to monitor for the development of resistance (change in resistant alleles' frequency) to Cry1F in field populations of FAW; and to provide a better understanding on the mode of action of the Cry1F toxin in the control of FAW.

BRIEF DESCRIPTION OF THE FIGURES

FIG. 1 is a mortality curve from reciprocal crosses of FAW from FAW-SPR to susceptible FAW as described in Example 5.

FIG. 2 is a mortality curve from Sr, rr FAW and backcrosses of rS to a FAW as described in Example 5.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Insect colonies resistant to toxins in general provide a great means to evaluate risks associated with resistance evolution, validate resistance management strategies, and improve resistance management practices. Furthermore, they serve as powerful tool for elucidating several aspects related to insecticide resistance, including the mode of action of insecticides, predicting or determining the mechanism of insect resistance, understanding the genetics associated with insect resistance, and for the discovery or design of new insect control tactics that will minimize the possibility of cross-resistant to existing control technologies. Traditional methods of creating insect resistance to a control tactic involve exposure of laboratory-adapted susceptible strains (or field collected susceptible insect populations) to increasing concentrations of the toxin on artificial diet, and maintaining any survivors after every generation of exposure. Disadvantages associated with this technique include the large number of individuals required to generate the colony, especially if the frequency of resistance alleles are extremely rare in the population. Moreover, because the selection pressure applied to laboratory-selected colonies is generally lower than what is observed in the field, often times this type of regime selects for individuals that do not necessarily reproduce mechanisms of resistance that will likely develop under field conditions.

The availability of insect colonies with developed resistance to chemical insecticides, or plant-incorporated protectants, in case of transgenic plants expressing insecticidal toxins, aids in understanding the relative importance of any changes in susceptibility detected in field populations through routine monitoring. Furthermore, it provides researchers with the opportunity to improve the sensitivity of monitoring techniques by identifying the gene or genes responsible for resistance (e.g. use of high-throughput molecular tools to detect the presence of resistant genes in field populations from different geographies, and monitor changes in allele frequency). Additionally, information generated from such colonies are particularly valuable as input parameters in modeling attempts.

The availability of a field-derived selected FAW colony that survives exposure to leaf material expressing Cry1F toxin is especially useful in evaluating such risks, as well as validating and improving resistance management. Because the FAW-SPR was selected for Cry1F resistance in the field, information generated from this colony will especially be field relevant and will improve our ability to mitigate resistance development to preserve the durability of TC1507 in geographic areas where resistance alleles are still found in lower frequency.

The present invention discloses the production of a fall armyworm colony from several hundred egg collected in corn fields in Puerto Rico in October 2008 and January 2009. Because of the origin of the eggs in Puerto Rico, the colony has been named the "Selected Puerto Rico Colony" which is referred to here as "FAW-SPR". FAW from this colony comprises field-evolved resistant to Cry1F.

As used herein, "field-evolved resistance to Cry1F" means a heritable trait of FAW that confers on the FAW enhanced tolerance to the insecticidal effects of Cry1F and that originated from an agricultural field or other non-laboratory environment. An FAW that displays the field-evolved resistance to Cry1F will be able to survive on diet comprising a higher concentration of Cry1F than a susceptible FAW that does not express the resistance trait. In one embodiment of the invention, the field-evolved resistance to Cry1F FAW will be due to a single gene or genetic locus, and in other embodiments, two or more genes can be involved. Moreover, it is recognized that the field-evolved resistance can be dominant, semi-dominant, or recessive. In one embodiment of the invention, a field-derived colony of FAW comprising field-evolved resistance to Cry1F was produced by methods of the present and invention and the field-evolved resistance to Cry1F was determined to be due to a single gene or genetic locus and the resistance was recessive. Thus, only FAW that are homozygous for the resistance allele display enhanced resistance to Cry1F, when compared to similar FAW that lack two copies of the resistance allele.

As used herein, "susceptible FAW", or "susceptible fall armyworm" or "susceptible individuals" means a fall armyworm (or army worms) that do not display that enhanced tolerance to Cry1F as disclosed herein.

The present invention relates to the production of a fall armyworm colony comprising field-evolved resistance to the insecticidal protein Cry1F. Because the resistance to Cry1F evolved in an agricultural field, it is believed that the use of such FAW in methods, for example, for developing resistance management strategies, is more advantageous than the use of resistant FAW that was produced via a laboratory-based, artificial-selection procedure. Thus, the field-derived FAW colonies of the present invention find use a number of improved methods related to, for example, resistance management and understanding the mechanism of fall armyworm resistance to Cry1F.

The present invention discloses the production of a field-derived colony of fall armyworm (FAW, *Spodoptera frugiperda*) selected for decreased susceptibility to maize plants expressing the insecticidal protein Cry1F. Thus, in one aspect the invention provides methods for producing a field-derived colony of FAW that comprises decreased susceptibility to maize plants producing Cry1F. FAW from such a field-derived colony comprise field-evolved resistance to Cry1F.

The methods for producing a field-derived colony of FAW that comprises decreased susceptibility to maize plants producing Cry1F involve collecting FAW, preferably FAW comprising resistance to Cry1F, from a field, particularly an agricultural field comprising one or more maize plants, more particularly an agricultural field comprising one or more maize plants that express the insecticidal protein Cry1F, most particularly an agricultural field comprising one or more maize plants comprising event TC1507. Maize plants comprising event TC1507 are transgenic maize plants that produce in their leaves Cry1F from a transgene comprising a maize ubiquitin (Ubi-1) gene promoter operably linked to a DNA molecule encoding a *Bacillus* delta-endotoxin identified as Cry1F. Maize plants comprising event TC1507 have been previously disclosed. See, U.S. Pat. Nos. 7,449,564; 7,435,807; 7,417,132; and 7,288,643; all of which are hereby incorporated in their entirety by reference. Cry1F has also been previously disclosed. See, U.S. Pat. Nos. 5,188,960 and 6,218,188; both of which are hereby incorporated in their entirety by reference.

Typically, the FAW will be collected from one or more agricultural fields in which the evolution of resistant FAW is suspected because of the observation of increased numbers of FAW in such agricultural fields which is indicative of the evolution of resistance in a population of maize plants previously comprised only susceptible FAW.

The FAW can be collected at any life stage (e.g., egg, larvae, pupa, and adult) although it is preferable to collect eggs as a matter of convenience. If eggs are collected, they can be hatched and resulting larva (neonates) allowed to feed on a diet comprising Cry1F at an effective concentration that is sufficient to kill all susceptible FAW but not FAW with field-evolved resistance. In a preferred embodiment of the invention, the larvae are fed leaf material from maize plants that express Cry1F, particularly maize plants comprising maize event TC1507.

It is recognized that an effective concentration of Cry1F can be determined by methods know in the art involving varying the concentration of Cry1F fed to both susceptible and resistant individuals and counting survivors after a certain period of exposure. It is recognized that methods can be also be used to determine $LC_{50}$, which is the lethal concentration at which 50% of individuals exposed to Cry1F do not survive.

The larvae (neonates) are allowed to feed on the Cry1F-containing diet for a period time sufficient to kill susceptible larvae and the surviving FAW selected. Generally, the period of time the larvae are exposed to the Cry1F-containing diet is at least 1, 2, 3, 4, 5, 6, 7, or more days, preferably between 2 and 6 days, more preferably between 3 and 5 days, most preferably 4 days.

The methods of the invention can further involve transfer of the surviving FAW to a standard fall armyworm diet that lacks Cry1F to allow the survivors to complete development. Such a diet can, for example, comprise maize leaf material that does not comprise Cry1F.

The methods can further involve allowing the surviving FAW to mate to maintain the colony with a secondary selection periodically applied in subsequent generations by feeding the FAW a diet as described above that comprises Cry1F at an effective concentration that is sufficient to kill all susceptible FAW but not FAW with field-evolved resistance from maize plants that express Cry1F. The methods can further involve selecting surviving FAW.

Typically, this secondary selection to maintain the field-evolved resistance in the colony will be applied every third generation although the invention does not depend on applying a secondary selection at a particular generation. The secondary selection only need be applied frequently enough to maintain to field-evolved resistance in the colony. Thus, the secondary selection can be applied to each generation, to the second generation, the third generation, the fourth generation, the fifth generation, or an even later generation.

In one embodiment, the methods of the present invention were used to produce a field-derived colony of FAW, referred to herein as "FAW-SPR", from eggs collected in Puerto Rico, USA in a field of transgenic maize plants comprising maize event TC1507. The FAW from this colony display decreased susceptibility to maize plants comprising maize event TC1507. The FAW-SPR colony was produced essentially as follows.
1. The Selected Puerto Rico Colony of fall armyworm (FAW-SPR) was initiated by collecting at least 1000 fall armyworm eggs from fields comprising maize plants comprising maize event TC1507 in Puerto Rico in October 2008 and January 2009.
2. Upon arrival at the laboratory, the eggs were incubated at approximate 25° C. until hatching. Hatching occurred within 1 day.
3. The recently hatched larvae (neonates) were exposed to Cry1F expressing leaf disks and allowed to grow for 4 days.
4. Survivors were collected and transferred to a standard fall armyworm diet lacking Cry1F (e.g., isoline corn) and allowed to complete development.
5. Individuals completing development are allowed to mate in order to maintain the colony.
6. Every three generations, selection in Cry1F expressing leaf tissue is conducted using a population of at least 500 neonates.

The present invention further provides methods for determining the inheritance of resistance of in a field-derived colony of FAW that comprises field-evolved resistance to Cry1F. The methods involve mating resistant FAW from the field-derived colony with FAW that are susceptible to Cry1F, preferably in reciprocal crosses, and analyzing the mortality rates of the progeny from each mating when grown in the presence of Cry1F. The methods can also involve backcrossing the progeny from each mating to resistant FAW. Such methods can be used to determine if the resistance to Cry1F is dominant, semi-dominant, or recessive or if sex-linkage is involved and can also be used to determine the number of resistance genes.

The present invention further provides methods for determining the frequency of resistance alleles in a population in which resistance has not evolved. The methods involve collecting insects of a insect pest of interest from a field or other non-laboratory site, mating virgin adults from the collected insects with virgin adults from resistant insects from a field-derived colony of the insect pest of interest whereby progeny larvae are produced and wherein the resistant insects comprise resistance to an insecticidal toxin, allowing the progeny larvae from the mating to feed on a diet comprising the insecticidal toxin at a concentration that is lethal to susceptible insects of insect pest of interest but not lethal to resistant insects of insect pest of interest, and determining mortality. Such methods find use, for example, in the development of resistance management strategies.

In one embodiment of the present invention, the methods for determining the frequency of resistance alleles in a population in which resistance has not evolved comprise collecting FAW from a field or other non-laboratory site, mating virgin adults from the collected FAW with virgin adults from the resistant FAW from the field-derived colony, allowing larvae from the mating to feed on a diet comprising Cry1F at a concentration that is lethal to susceptible FAW but not lethal to resistant FAW, and determining mortality. Such methods find use, for example, in the development of resistance management strategies.

The present invention further provides methods of using a field-derived colony of an insect pest of interest that comprises an insect pest of interest with field-evolved resistance to an insecticidal toxin that is expressed in a transgenic plant, particular a transgenic crop plant. Such a field-derived colony of an insect pest of interest can be produced, for example, by the methods disclosed herein or by any other method known in the art. Such field-derived colonies include, for example, those disclosed in Tabashnik et al. ((2009) *J. Econ. Entomol.* 102:2011-2025).

The methods of the invention include, for example, using such a field-derived colony of an insect pest of interest in methods: for understanding the mechanism of the insect resistance to insecticidal toxin; for evaluating cross-resistance potential of the insecticidal toxin with any other existing or new insecticides or insecticidal proteins with activity against the insect pest of interest; to improve resistance monitoring strategies for the insect pest of interest in geographic locations where crop plants expressing the insecticidal toxin have been commercialized or are planned to be commercialized; of validating assumptions used in known resistance-risk computer simulation models for crop plants expressing the insecticidal toxin; for evaluating alternative refuge deployment strategies for crop plants, such as, for example, seed mixes or refuge-in-a-bag strategies; of investigating whether or not existing insect control tactics will affect the rate at which the insect pest of interest may develop resistance to transgenic crop plants expressing the insecticidal toxin under field conditions; to develop molecular marker technology to monitor for the development of resistance (change in resistant alleles' frequency) to the insecticidal toxin in field populations of the insect pest of interest; and to provide a better understanding on the mode of action of the insecticidal toxin in the control of the insect pest of interest.

The present invention further provides methods of using a field-derived colony of FAW that comprises FAW with field-evolved resistance to Cry1F. Such a field-derived colony of FAW can be produced, for example, by the methods disclosed herein or by any other method know in the art. In general such methods relate to the management of resistance to FAW in maize plants comprising Cry1F and to understanding the mechanism of fall armyworm resistance to Cry1F. A number of such methods of using a field-derived colony of FAW that comprises FAW with field-evolved resistance to Cry1F are disclosed below, although many modifications and other embodiments of the methods set forth herein will come to mind to one skilled in the art to which these inventions pertain having the benefit of the teachings presented in the foregoing descriptions and the associated drawings.

The methods of the invention include, but are not limited to, using a field-derived colony of FAW that comprises FAW with field-evolved resistance to Cry1F:

1. To understand the mechanism of fall armyworm resistance to Cry1F. This information will assist in the design and development of novel tactics for fall armyworm resistance management. The most frequent mechanism of *B. thuringiensis* toxins resistance is binding site modification, which has been shown to be the basis of cross-resistance among Cry1A toxins (Ferré and J. Van Rie (2002) *Annu. Rev. Entomol.* 47:501-533). From a resistance management perspective, toxins that act on the same binding sites should not be used as complements or replacements for each other. For example, several insect species have shown common binding sites for Cry1A and Cry1Ja, apparently a general pattern in lepidopteran species (Hua et al. (2001) *App. Environ. Microbiol.* 67:872-879). Hernandes and Ferré ((2005) *Appl. Environ. Entomol.* 71:5627-5629) have shown that *Helicoverpa armigera, Helicoverpa zea*, and *Spodoptera exigua* share a common receptor for Cry1Ac, Cry1Fa, and Cry1Ja through binding studies using $^{125}$I-Cry1Ac and biotinylated Cry1Fa toxins. This study was conducted using susceptible laboratory strains. The availability of a field derived FAW resistance strain will allow, for example, for the generation of field-relevant information that may assist in the development of resistance management strategies.

2. To evaluate cross-resistance potential of Cry1F with any other existing or new insecticides or insecticidal proteins with activity against fall armyworm. This information will assist in the development of new product concepts as single traits or in combination with TC1507 to minimize the likelihood of resistance development in areas where resistance has not evolved. Cross-resistance studies with new actives are commonly conducted using diet-based bioassays as described by Pereira et al ((2008) *Entomologia Experimentalis et Applicata* 126: 115-121) and Siqueira et al. ((2004) *J. Pest Manag. Sci.* 90:1189-1196.

3. To evaluate cross-resistance potential of TC1507 with any current fall armyworm actives that may be used in combination to TC1507 to minimize the likelihood of resistance development in areas where resistance has not evolved. Cross-resistance studies with commercially available actives are commonly conducted using diet-based bioassays or tissue-based bioassays as described by Pereira et al ((2008) *Entomologia Experimentalis et Applicata* 126:115-121), Siqueira et al. ((2004) *J. Pest Manag. Sci.* 90:1189-1196, and Crespo et al. ((2009) *Pest Manag Sci.* 65:1071-1081).

4. To improve fall armyworm resistance monitoring strategies for TC1507 in maize in the continental U.S.A. and other geographic locations where event TC1507 is or will be commercialized, FAW is a major pest and resistance has not evolved. This can be done by estimating frequency of resistance alleles in populations where resistance has not evolved using either an F1 or F2 screen, as described by Gould et al. ((1997) *PNAS* 94:3519-3523) and Andow and Alstad ((1998) *J. Econ. Entomol.* 91:572-578), respectively.

5. To validate assumptions used in the resistance-risk computer simulation model for event TC1507. For example, computer simulations based on empirically derived parameters, such as mortality and dispersal estimates, would serve as an improved tool to better indicate whether different refuge deployment strategies would have an impact in delaying the evolution of resistance in different insect population species (Davis and Onstad 2000). Empirically derived parameters obtained from both susceptible and resistance strains will strengthen predictions generated by computer simulations.

6. To evaluate alternative refuge deployment strategies for TC1507 maize, such as seed mixes or refuge-in-a-bag. In designing functional refuge deployment strategies, some of the aspects that one must take into account include the biology of the insect pest in question and also aspects specific to insect-plant interactions. For example, there are two FAW strains (rice and maize strains) that are morphologically identical but genetically distinct. These strains also differ physiologically and behaviorally. A better understanding of the biology of these host strains would serve as a tool to more accurately generate predictions of fall armyworm population behavior in the field (Nagoshi and Meagher (2004) *Florida Entomol.* 87:440-449). Another behavioral component that is important in designing refuge deployment strategies is insect dispersal both in larval and adult stages. Adult dispersal patterns may have an impact on random mating of susceptible and potential resistance individuals that emerge from transgenic fields, depending on refuge placement (Hunt et al. (2001) *J. Econ. Entomol.* 94:1369-1377). Also, while considering seed mix as a refuge strategy, one must take into account whether differential survival of heterozygous insects would favored in case of larval movement between plants (Davis and Onstad (2000) *J. Econ. Entomol.* 93:937-948).

7. To investigate whether or not existing fall armyworm control tactics, namely MON810, Bt11, MIR162, and chemical insecticides, will affect the rate at which fall armyworm may develop resistance to TC1507 under natural field conditions. This information would be generated based on the presence or absence of cross-resistance between or across insect control tactics used in the geographic locations in question.

8. To develop molecular marker technology to monitor for development of resistance (change in resistant alleles' frequency) in field populations. This can be done by estimating frequency of resistance alleles in populations where resistance has not evolved using either an F1 or F2 screen, as described by Gould et al. ((1997) *PNAS* 94:3519-3523) and Andow and Alstad ((1998) *J. Econ. Entomol.* 91:572-578), respectively.

9. To provide a better understanding on the mode of action of Cry1F toxin in the control of FAW. It is generally accepted that steps involved in Bt mode of action include toxin solubilization, enzymatic activation, and binding to midgut receptors (Knowles (1994) *Advances Insect Physiol.* 24:275-308; Schnepf et al. (1998) *Microbiol. Mol. Biol. Rev.* 62:775-806; Bravo et al. (2007) *Toxicon* 49:423-435). Each of the several steps involved in Bt mode of action represent an opportunity for insect adaptation that could result in reduced susceptibility or even complete resistance to Bt exposure (Schnepf et al. (1998) *Microbiol. Mol. Biol. Rev.* 62:775-806; Ferré and J. Van Rie (2002) *Annu. Rev. Entomol.* 47:501-533; Bravo and Soberón (2008) *Trends Biotechnol.* 26:573-579). Reduced susceptibility also could manifest itself in the form of gut regeneration, toxin sequestration or behavioral modification (Lockwood et al. (1984) *Bull. Entomological Soc. America* 30:41-51; Heckel et al. (2007) *J. Invertebrate Pathol.* 95:192-197). Nevertheless, receptor alterations are the most frequently reported form of Bt resistance (Ferré and J. Van Rie (2002) *Annu. Rev. Entomol.* 47:501-533). Bt mode of action is complex and pathways of toxicity cannot be defined by any single technique. Clearly differentiating the mode of action of one toxin from another can require a combination of approaches such as structural analyses, receptor binding studies (Hua et al. (2001) *Appl. Environ. Microbiol.* 67:872-879; Sena et al. (2009) *Appl. Environ. Microbiol.* 75:2236-2237), pore formation studies (Chen et al. (1993) *PNAS* 90:9041-9045; Lee et al. (2003) *Appl. Environ. Entomol.* 69:4648-4657), and cross-resistance assessments (Pereira et al. (2008) *Entomologia Experimentalis et Applicata* 126:115-121; Hernández-Martínez et al. (2009) *Pest Manag. Sci.* 65:645-650).

It is recognized that methods of using a field-derived colony of FAW disclosed herein above and below can be used with other insect pests of interest that have evolved resistance in the field to one or more insecticidal toxins that are expressed in at least one plant, particular crop plants, more particularly transgenic crop plants that express an insecticidal toxin such as, for example, a Bt toxin.

Insect pests of interest of the present invention include, but are not limited to, insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira (Xylomyges) curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* J E Smith (fall armyworm); *S. exigua* Hubner (beet armyworm); *S. litura* Fabricius (tobacco cutworm, cluster caterpillar); *Trichoplusia ni* Hubner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape colaspis); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leafmining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); Blostomatidae spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); Cimicidae spp.; Coreidae spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and Hyalopterus pruni Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); Reduviidae spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptacoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); Tinidae spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cornitermes cumulans* Kollar, *Cylindrotermes nordenskioeldi* Holmgren and *Pseudacanthotermes militaris* Hagen (sugarcane termite); as well as those in the Rhinotermitidae family including, but not limited to *Heterotermes tenuis* Hagen. Insects of the order Thysanoptera are also of interest, including but not limited to thrips, such as *Stenchaetothrips minutus* van Deventer (sugarcane thrips).

The present invention with any plant species that expresses an insecticidal toxin, particularly transgenic plants that have been engineered to express an insecticidal toxin, more particularly crop plants that have been engineered to express an insecticidal toxi. Plant species of the invention include, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and cotton plants are optimal, and in yet other embodiments corn plants are optimal.

The methods of the present invention can be used with any insecticidal toxin that can be expressed in a plant to provide resistance to the plant to one or more insect pests of the invention. In some embodiments, the insecticidal protein is a δ-endotoxin of *Bacillus* spp. or derivatives thereof that comprise insecticidal activity. Such δ-endotoxin and synthetic derivatives are referred to herein as Bt toxins. The specific activity of Bt toxins is considered highly beneficial. Unlike most insecticides, the Bt toxins do not have a broad spectrum of activity, so they typically do not kill beneficial insects. Furthermore, the Bt toxins are non-toxic to mammals, including humans, domesticated animals, and wildlife. In particular embodiments, the Bt toxins is a Cry protein.

A list of some known δ-endotoxins (Cry and Cyt endotoxins) and their GenBank Accession Numbers are listed in Table 1. Any of these insecticidal toxins can be expressed in a plant and used as the insecticidal toxin in methods disclosed herein. Moreover, it is recognized that derivatives of any one or more of these insecticidal proteins can be made using method known in the art such as for example DNA shuffling to produce insecticidal toxins comprising, for example, increased insecticidal activity against a pest of interest and/or to alter the target pest specificity of the insecticidal toxin. The use of such derivatives in the methods disclosed here is encompassed by the present invention.

TABLE 1

Some Known δ-endotoxins and their GenBank ® Accession Nos.

| Endotoxin | GenBank ® Accession No. |
| --- | --- |
| Cry1Aa1 | AAA22353 |
| Cry1Aa2 | AAA22552 |
| Cry1Aa3 | BAA00257 |
| Cry1Aa4 | CAA31886 |
| Cry1Aa5 | BAA04468 |
| Cry1Aa6 | AAA86265 |
| Cry1Aa7 | AAD46139 |
| Cry1Aa8 | I26149 |
| Cry1Aa9 | BAA77213 |
| Cry1Aa10 | AAD55382 |
| Cry1Aa11 | CAA70856 |
| Cry1Aa12 | AAP80146 |
| Cry1Aa13 | AAM44305 |
| Cry1Aa14 | AAP40639 |
| Cry1Aa15 | AAY66993 |
| Cry1Ab1 | AAA22330 |
| Cry1Ab2 | AAA22613 |
| Cry1Ab3 | AAA22561 |
| Cry1Ab4 | BAA00071 |
| Cry1Ab5 | CAA28405 |
| Cry1Ab6 | AAA22420 |
| Cry1Ab7 | CAA31620 |
| Cry1Ab8 | AAA22551 |
| Cry1Ab9 | CAA38701 |
| Cry1Ab10 | A29125 |
| Cry1Ab11 | I12419 |
| Cry1Ab12 | AAC64003 |
| Cry1Ab13 | AAN76494 |
| Cry1Ab14 | AAG16877 |
| Cry1Ab15 | AAO13302 |
| Cry1Ab16 | AAK55546 |
| Cry1Ab17 | AAT46415 |
| Cry1Ab18 | AAQ88259 |
| Cry1Ab19 | AAW31761 |
| Cry1Ab20 | ABB72460 |
| Cry1Ab21 | ABS18384 |
| Cry1Ab22 | ABW87320 |
| Cry1Ab-like | AAK14336 |
| Cry1Ab-like | AAK14337 |
| Cry1Ab-like | AAK14338 |
| Cry1Ab-like | ABG88858 |
| Cry1Ac1 | AAA22331 |
| Cry1Ac2 | AAA22338 |

TABLE 1-continued

Some Known δ-endotoxins and their GenBank ® Accession Nos.

| Endotoxin | GenBank ® Accession No. |
| --- | --- |
| Cry1Ac3 | CAA38098 |
| Cry1Ac4 | AAA73077 |
| Cry1Ac5 | AAA22339 |
| Cry1Ac6 | AAA86266 |
| Cry1Ac7 | AAB46989 |
| Cry1Ac8 | AAC44841 |
| Cry1Ac9 | AAB49768 |
| Cry1Ac10 | CAA05505 |
| Cry1Ac11 | CAA10270 |
| Cry1Ac12 | I12418 |
| Cry1Ac13 | AAD38701 |
| Cry1Ac14 | AAQ06607 |
| Cry1Ac15 | AAN07788 |
| Cry1Ac16 | AAU87037 |
| Cry1Ac17 | AAX18704 |
| Cry1Ac18 | AAY88347 |
| Cry1Ac19 | ABD37053 |
| Cry1Ac20 | ABB89046 |
| Cry1Ac21 | AAY66992 |
| Cry1Ac22 | ABZ01836 |
| Cry1Ac23 | CAQ30431 |
| Cry1Ac24 | ABL01535 |
| Cry1Ac25 | FJ513324 |
| Cry1Ac26 | FJ617446 |
| Cry1Ac27 | FJ617447 |
| Cry1Ac28 | ACM90319 |
| Cry1Ad1 | AAA22340 |
| Cry1Ad2 | CAA01880 |
| Cry1Ae1 | AAA22410 |
| Cry1Af1 | AAB82749 |
| Cry1Ag1 | AAD46137 |
| Cry1Ah1 | AAQ14326 |
| Cry1Ah2 | ABB76664 |
| Cry1Ai1 | AAO39719 |
| Cry1A-like | AAK14339 |
| Cry1Ba1 | CAA29898 |
| Cry1Ba2 | CAA65003 |
| Cry1Ba3 | AAK63251 |
| Cry1Ba4 | AAK51084 |
| Cry1Ba5 | ABO20894 |
| Cry1Ba6 | ABL60921 |
| Cry1Bb1 | AAA22344 |
| Cry1Bc1 | CAA86568 |
| Cry1Bd1 | AAD10292 |
| Cry1Bd2 | AAM93496 |
| Cry1Be1 | AAC32850 |
| Cry1Be2 | AAQ52387 |
| Cry1Be3 | FJ716102 |
| Cry1Bf1 | CAC50778 |
| Cry1Bf2 | AAQ52380 |
| Cry1Bg1 | AAO39720 |
| Cry1Ca1 | CAA30396 |
| Cry1Ca2 | CAA31951 |
| Cry1Ca3 | AAA22343 |
| Cry1Ca4 | CAA01886 |
| Cry1Ca5 | CAA65457 |
| Cry1Ca6 | AAF37224 |
| Cry1Ca7 | AAG50438 |
| Cry1Ca8 | AAM00264 |
| Cry1Ca9 | AAL79362 |
| Cry1Ca10 | AAN16462 |
| Cry1Ca11 | AAX53094 |
| Cry1Cb1 | M97880 |
| Cry1Cb2 | AAG35409 |
| Cry1Cb3 | ACD50894 |
| Cry1Cb-like | AAX63901 |
| Cry1Da1 | CAA38099 |
| Cry1Da2 | I76415 |
| Cry1Db1 | CAA80234 |
| Cry1Db2 | AAK48937 |
| Cry1Dc1 | ABK35074 |
| Cry1Ea1 | CAA37933 |
| Cry1Ea2 | CAA39609 |
| Cry1Ea3 | AAA22345 |
| Cry1Ea4 | AAD04732 |
| Cry1Ea5 | A15535 |

TABLE 1-continued

Some Known δ-endotoxins and their GenBank ® Accession Nos.

| Endotoxin | GenBank ® Accession No. |
|---|---|
| Cry1Ea6 | AAL50330 |
| Cry1Ea7 | AAW72936 |
| Cry1Ea8 | ABX11258 |
| Cry1Eb1 | AAA22346 |
| Cry1Fa1 | AAA22348 |
| Cry1Fa2 | AAA22347 |
| Cry1Fb1 | CAA80235 |
| Cry1Fb2 | BAA25298 |
| Cry1Fb3 | AAF21767 |
| Cry1Fb4 | AAC10641 |
| Cry1Fb5 | AAO13295 |
| Cry1Fb6 | ACD50892 |
| Cry1Fb7 | ACD50893 |
| Cry1Ga1 | CAA80233 |
| Cry1Ga2 | CAA70506 |
| Cry1Gb1 | AAD10291 |
| Cry1Gb2 | AAO13756 |
| Cry1Gc | AAQ52381 |
| Cry1Ha1 | CAA80236 |
| Cry1Hb1 | AAA79694 |
| Cry1H-like | AAF01213 |
| Cry1Ia1 | CAA44633 |
| Cry1Ia2 | AAA22354 |
| Cry1Ia3 | AAC36999 |
| Cry1Ia4 | AAB00958 |
| Cry1Ia5 | CAA70124 |
| Cry1Ia6 | AAC26910 |
| Cry1Ia7 | AAM73516 |
| Cry1Ia8 | AAK66742 |
| Cry1Ia9 | AAQ08616 |
| Cry1Ia10 | AAP86782 |
| Cry1Ia11 | CAC85964 |
| Cry1Ia12 | AAV53390 |
| Cry1Ia13 | ABF83202 |
| Cry1Ia14 | ACG63871 |
| Cry1Ia15 | FJ617445 |
| Cry1Ia16 | FJ617448 |
| Cry1Ib1 | AAA82114 |
| Cry1Ib2 | ABW88019 |
| Cry1Ib3 | ACD75515 |
| Cry1Ic1 | AAC62933 |
| Cry1Ic2 | AAE71691 |
| Cry1Id1 | AAD44366 |
| Cry1Ie1 | AAG43526 |
| Cry1If1 | AAQ52382 |
| Cry1I-like | AAC31094 |
| Cry1I-like | ABG88859 |
| Cry1Ja1 | AAA22341 |
| Cry1Jb1 | AAA98959 |
| Cry1Jc1 | AAC31092 |
| Cry1Jc2 | AAQ52372 |
| Cry1Jd1 | CAC50779 |
| Cry1Ka1 | AAB00376 |
| Cry1La1 | AAS60191 |
| Cry1-like | AAC31091 |
| Cry2Aa1 | AAA22335 |
| Cry2Aa2 | AAA83516 |
| Cry2Aa3 | D86064 |
| Cry2Aa4 | AAC04867 |
| Cry2Aa5 | CAA10671 |
| Cry2Aa6 | CAA10672 |
| Cry2Aa7 | CAA10670 |
| Cry2Aa8 | AAO13734 |
| Cry2Aa9 | AAO13750 |
| Cry2Aa10 | AAQ04263 |
| Cry2Aa11 | AAQ52384 |
| Cry2Aa12 | ABI83671 |
| Cry2Aa13 | ABL01536 |
| Cry2Aa14 | ACF04939 |
| Cry2Ab1 | AAA22342 |
| Cry2Ab2 | CAA39075 |
| Cry2Ab3 | AAG36762 |
| Cry2Ab4 | AAO13296 |
| Cry2Ab5 | AAQ04609 |
| Cry2Ab6 | AAP59457 |
| Cry2Ab7 | AAZ66347 |
| Cry2Ab8 | ABC95996 |
| Cry2Ab9 | ABC74968 |
| Cry2Ab10 | EF157306 |
| Cry2Ab11 | CAM84575 |
| Cry2Ab12 | ABM21764 |
| Cry2Ab13 | ACG76120 |
| Cry2Ab14 | ACG76121 |
| Cry2Ac1 | CAA40536 |
| Cry2Ac2 | AAG35410 |
| Cry2Ac3 | AAQ52385 |
| Cry2Ac4 | ABC95997 |
| Cry2Ac5 | ABC74969 |
| Cry2Ac6 | ABC74793 |
| Cry2Ac7 | CAL18690 |
| Cry2Ac8 | CAM09325 |
| Cry2Ac9 | CAM09326 |
| Cry2Ac10 | ABN15104 |
| Cry2Ac11 | CAM83895 |
| Cry2Ac12 | CAM83896 |
| Cry2Ad1 | AAF09583 |
| Cry2Ad2 | ABC86927 |
| Cry2Ad3 | CAK29504 |
| Cry2Ad4 | CAM32331 |
| Cry2Ad5 | CAO78739 |
| Cry2Ae1 | AAQ52362 |
| Cry2Af1 | ABO30519 |
| Cry2Ag | ACH91610 |
| Cry2Ah | EU939453 |
| Cry2Ah2 | ACL80665 |
| Cry2Ai | FJ788388 |
| Cry3Aa1 | AAA22336 |
| Cry3Aa2 | AAA22541 |
| Cry3Aa3 | CAA68482 |
| Cry3Aa4 | AAA22542 |
| Cry3Aa5 | AAA50255 |
| Cry3Aa6 | AAC43266 |
| Cry3Aa7 | CAB41411 |
| Cry3Aa8 | AAS79487 |
| Cry3Aa9 | AAW05659 |
| Cry3Aa10 | AAU29411 |
| Cry3Aa11 | AAW82872 |
| Cry3Aa12 | ABY49136 |
| Cry3Ba1 | CAA34983 |
| Cry3Ba2 | CAA00645 |
| Cry3Bb1 | AAA22334 |
| Cry3Bb2 | AAA74198 |
| Cry3Bb3 | I15475 |
| Cry3Ca1 | CAA42469 |
| Cry4Aa1 | CAA68485 |
| Cry4Aa2 | BAA00179 |
| Cry4Aa3 | CAD30148 |
| Cry4A-like | AAY96321 |
| Cry4Ba1 | CAA30312 |
| Cry4Ba2 | CAA30114 |
| Cry4Ba3 | AAA22337 |
| Cry4Ba4 | BAA00178 |
| Cry4Ba5 | CAD30095 |
| Cry4Ba-like | ABC47686 |
| Cry4Ca1 | EU646202 |
| Cry4Cb1 | FJ403208 |
| Cry4Cb2 | FJ597622 |
| Cry4Cc1 | FJ403207 |
| Cry5Aa1 | AAA67694 |
| Cry5Ab1 | AAA67693 |
| Cry5Ac1 | I34543 |
| Cry5Ad1 | ABQ82087 |
| Cry5Ba1 | AAA68598 |
| Cry5Ba2 | ABW88932 |
| Cry6Aa1 | AAA22357 |
| Cry6Aa2 | AAM46849 |
| Cry6Aa3 | ABH03377 |
| Cry6Ba1 | AAA22358 |
| Cry7Aa1 | AAA22351 |
| Cry7Ab1 | AAA21120 |
| Cry7Ab2 | AAA21121 |
| Cry7Ab3 | ABX24522 |

TABLE 1-continued

Some Known δ-endotoxins and their GenBank® Accession Nos.

| Endotoxin | GenBank® Accession No. |
|---|---|
| Cry7Ab4 | EU380678 |
| Cry7Ab5 | ABX79555 |
| Cry7Ab6 | ACI44005 |
| Cry7Ab7 | FJ940776 |
| Cry7Ab8 | GU145299 |
| Cry7Ba1 | ABB70817 |
| Cry7Ca1 | ABR67863 |
| Cry7Da1 | ACQ99547 |
| Cry8Aa1 | AAA21117 |
| Cry8Ab1 | EU044830 |
| Cry8Ba1 | AAA21118 |
| Cry8Bb1 | CAD57542 |
| Cry8Bc1 | CAD57543 |
| Cry8Ca1 | AAA21119 |
| Cry8Ca2 | AAR98783 |
| Cry8Ca3 | EU625349 |
| Cry8Da1 | BAC07226 |
| Cry8Da2 | BD133574 |
| Cry8Da3 | BD133575 |
| Cry8Db1 | BAF93483 |
| Cry8Ea1 | AAQ73470 |
| Cry8Ea2 | EU047597 |
| Cry8Fa1 | AAT48690 |
| Cry8Ga1 | AAT46073 |
| Cry8Ga2 | ABC42043 |
| Cry8Ga3 | FJ198072 |
| Cry8Ha1 | EF465532 |
| Cry8Ia1 | EU381044 |
| Cry8Ja1 | EU625348 |
| Cry8Ka1 | FJ422558 |
| Cry8Ka2 | ACN87262 |
| Cry8-like | FJ770571 |
| Cry8-like | ABS53003 |
| Cry9Aa1 | CAA41122 |
| Cry9Aa2 | CAA41425 |
| Cry9Aa3 | GQ249293 |
| Cry9Aa4 | GQ249294 |
| Cry9Aa like | AAQ52376 |
| Cry9Ba1 | CAA52927 |
| Cry9Bb1 | AAV28716 |
| Cry9Ca1 | CAA85764 |
| Cry9Ca2 | AAQ52375 |
| Cry9Da1 | BAA19948 |
| Cry9Da2 | AAB97923 |
| Cry9Da3 | GQ249295 |
| Cry9Da4 | GQ249297 |
| Cry9Db1 | AAX78439 |
| Cry9Ea1 | BAA34908 |
| Cry9Ea2 | AAO12908 |
| Cry9Ea3 | ABM21765 |
| Cry9Ea4 | ACE88267 |
| Cry9Ea5 | ACF04743 |
| Cry9Ea6 | ACG63872 |
| Cry9Ea7 | FJ380927 |
| Cry9Ea8 | GQ249292 |
| Cry9Eb1 | CAC50780 |
| Cry9Eb2 | GQ249298 |
| Cry9Ec1 | AAC63366 |
| Cry9Ed1 | AAX78440 |
| Cry9Ee1 | GQ249296 |
| Cry9-like | AAC63366 |
| Cry10Aa1 | AAA22614 |
| Cry10Aa2 | E00614 |
| Cry10Aa3 | CAD30098 |
| Cry10A-like | DQ167578 |
| Cry11Aa1 | AAA22352 |
| Cry11Aa2 | AAA22611 |
| Cry11Aa3 | CAD30081 |
| Cry11Aa-like | DQ166531 |
| Cry11Ba1 | CAA60504 |
| Cry11Bb1 | AAC97162 |
| Cry12Aa1 | AAA22355 |
| Cry13Aa1 | AAA22356 |
| Cry14Aa1 | AAA21516 |
| Cry15Aa1 | AAA22333 |
| Cry16Aa1 | CAA63860 |
| Cry17Aa1 | CAA67841 |
| Cry18Aa1 | CAA67506 |
| Cry18Ba1 | AAF89667 |
| Cry18Ca1 | AAF89668 |
| Cry19Aa1 | CAA68875 |
| Cry19Ba1 | BAA32397 |
| Cry20Aa1 | AAB93476 |
| Cry20Ba1 | ACS93601 |
| Cry20-like | GQ144333 |
| Cry21Aa1 | I32932 |
| Cry21Aa2 | I66477 |
| Cry21Ba1 | BAC06484 |
| Cry22Aa1 | I34547 |
| Cry22Aa2 | CAD43579 |
| Cry22Aa3 | ACD93211 |
| Cry22Ab1 | AAK50456 |
| Cry22Ab2 | CAD43577 |
| Cry22Ba1 | CAD43578 |
| Cry23Aa1 | AAF76375 |
| Cry24Aa1 | AAC61891 |
| Cry24Ba1 | BAD32657 |
| Cry24Ca1 | CAJ43600 |
| Cry25Aa1 | AAC61892 |
| Cry26Aa1 | AAD25075 |
| Cry27Aa1 | BAA82796 |
| Cry28Aa1 | AAD24189 |
| Cry28Aa2 | AAG00235 |
| Cry29Aa1 | CAC80985 |
| Cry30Aa1 | CAC80986 |
| Cry30Ba1 | BAD00052 |
| Cry30Ca1 | BAD67157 |
| Cry30Ca2 | ACU24781 |
| Cry30Da1 | EF095955 |
| Cry30Db1 | BAE80088 |
| Cry30Ea1 | ACC95445 |
| Cry30Ea2 | FJ499389 |
| Cry30Fa1 | ACI22625 |
| Cry30Ga1 | ACG60020 |
| Cry31Aa1 | BAB11757 |
| Cry31Aa2 | AAL87458 |
| Cry31Aa3 | BAE79808 |
| Cry31Aa4 | BAF32571 |
| Cry31Aa5 | BAF32572 |
| Cry31Ab1 | BAE79809 |
| Cry31Ab2 | BAF32570 |
| Cry31Ac1 | BAF34368 |
| Cry32Aa1 | AAG36711 |
| Cry32Ba1 | BAB78601 |
| Cry32Ca1 | BAB78602 |
| Cry32Da1 | BAB78603 |
| Cry33Aa1 | AAL26871 |
| Cry34Aa1 | AAG50341 |
| Cry34Aa2 | AAK64560 |
| Cry34Aa3 | AAT29032 |
| Cry34Aa4 | AAT29030 |
| Cry34Ab1 | AAG41671 |
| Cry34Ac1 | AAG50118 |
| Cry34Ac2 | AAK64562 |
| Cry34Ac3 | AAT29029 |
| Cry34Ba1 | AAK64565 |
| Cry34Ba2 | AAT29033 |
| Cry34Ba3 | AAT29031 |
| Cry35Aa1 | AAG50342 |
| Cry35Aa2 | AAK64561 |
| Cry35Aa3 | AAT29028 |
| Cry35Aa4 | AAT29025 |
| Cry35Ab1 | AAG41672 |
| Cry35Ab2 | AAK64563 |
| Cry35Ab3 | AY536891 |
| Cry35Ac1 | AAG50117 |
| Cry35Ba1 | AAK64566 |
| Cry35Ba2 | AAT29027 |
| Cry35Ba3 | AAT29026 |
| Cry36Aa1 | AAK64558 |
| Cry37Aa1 | AAF76376 |
| Cry38Aa1 | AAK64559 |

TABLE 1-continued

Some Known δ-endotoxins and their GenBank ® Accession Nos.

| Endotoxin | GenBank ® Accession No. |
|---|---|
| Cry39Aa1 | BAB72016 |
| Cry40Aa1 | BAB72018 |
| Cry40Ba1 | BAC77648 |
| Cry40Ca1 | EU381045 |
| Cry40Da1 | ACF15199 |
| Cry41Aa1 | BAD35157 |
| Cry41Ab1 | BAD35163 |
| Cry42Aa1 | BAD35166 |
| Cry43Aa1 | BAD15301 |
| Cry43Aa2 | BAD95474 |
| Cry43Ba1 | BAD15303 |
| Cry43-like | BAD15305 |
| Cry44Aa | BAD08532 |
| Cry45Aa | BAD22577 |
| Cry46Aa | BAC79010 |
| Cry46Aa2 | BAG68906 |
| Cry46Ab | BAD35170 |
| Cry47Aa | AAY24695 |
| Cry48Aa | CAJ18351 |
| Cry48Aa2 | CAJ86545 |
| Cry48Aa3 | CAJ86546 |
| Cry48Ab | CAJ86548 |
| Cry48Ab2 | CAJ86549 |
| Cry49Aa | CAH56541 |
| Cry49Aa2 | CAJ86541 |
| Cry49Aa3 | CAJ86543 |
| Cry49Aa4 | CAJ86544 |
| Cry49Ab1 | CAJ86542 |
| Cry50Aa1 | BAE86999 |
| Cry51Aa1 | ABI14444 |
| Cry52Aa1 | EF613489 |
| Cry52Ba1 | FJ361760 |
| Cry53Aa1 | EF633476 |
| Cry53Ab1 | FJ361759 |
| Cry54Aa1 | ACA52194 |
| Cry55Aa1 | ABW88931 |
| Cry55Aa2 | AAE33526 |
| Cry56Aa1 | FJ597621 |
| Cry56Aa2 | GQ483512 |
| Cry57Aa1 | ANC87261 |
| Cry58Aa1 | ANC87260 |
| Cry59Aa1 | ACR43758 |
| Cyt1Aa1 | X03182 |
| Cyt1Aa2 | X04338 |
| Cyt1Aa3 | Y00135 |
| Cyt1Aa4 | M35968 |
| Cyt1Aa5 | AL731825 |
| Cyt1Aa6 | ABC17640 |
| Cyt1Aa-like | ABB01172 |
| Cyt1Ab1 | X98793 |
| Cyt1Ba1 | U37196 |
| Cyt1Ca1 | AL731825 |
| Cyt2Aa1 | Z14147 |
| Cyt2Aa2 | AF472606 |
| Cyt2Aa3 | EU835185 |
| Cyt2Ba1 | U52043 |
| Cyt2Ba2 | AF020789 |
| Cyt2Ba3 | AF022884 |
| Cyt2Ba4 | AF022885 |
| Cyt2Ba5 | AF022886 |
| Cyt2Ba6 | AF034926 |
| Cyt2Ba7 | AF215645 |
| Cyt2Ba8 | AF215646 |
| Cyt2Ba9 | AL731825 |
| Cyt2Ba10 | ACX54358 |
| Cyt2Ba11 | ACX54359 |
| Cyt2Ba12 | ACX54360 |
| Cyt2Ba-like | ABE99695 |
| Cyt2Bb1 | U82519 |
| Cyt2Bc1 | CAC80987 |
| Cyt2B-like | DQ341380 |
| Cyt2Ca1 | AAK50455 |
| Unknown | AAA22332 |
| Unknown | AAL26870 |
| Unknown | CAA63374 |
| Unknown | BAA13073 |
| Unknown | CAA67205 |
| Unknown | CAA67329 |

The following examples are offered by way of illustration and not by way of limitation.

EXAMPLE 1

Production of Field-Derived Fall Armyworm Colony Selected for Decreased Susceptibility to Maize Plants Expressing the Insecticidal Protein Cry1F A fall armyworm colony exhibiting field-selected resistance to maize expressing event TC1507 was established in a laboratory. The process by which the colony was produced comprised the following steps.

1. The Selected Puerto Rico Colony (FAW-SPR) was initiated by collecting at least 1000 fall armyworm eggs from fields in Puerto Rico in October 2008 and again in January 2009.

2. Upon arrival at the laboratory, the eggs were incubated at approximate 25° C. until hatching. Hatching occurred within 1 day.

3. The recently hatched larvae (neonates) were exposed to Cry1F expressing leaf disks from maize plants comprising event TC1507 and allowed to grow for 4 days. The concentration of Cry1F in the leaf discs was 12.1±6.2 ng/mg leaf tissue dry weight.

4. Survivors were collected and transferred to a standard fall armyworm diet and allowed to complete development. Survivors from both the October 2008 and January 2009 collections were combined.

5. Individuals completing development are allowed to randomly mate in order to maintain the colony.

6. Every three generations, selection in Cry1F-expressing leaf tissue from maize plants comprising event TC1507 is conducted using a population of at least 500 neonates.

EXAMPLE 2

Characterization of Cry1F Resistance in Fall Armyworm Using a Field-Derived Colony A study was conducted to characterize the susceptibility of the Puerto Rico Colony to Cry1F using a diagnostic assay. Characterization of the FAW-SPR susceptibility to the Bt Cry1F insecticidal toxin was assessed by measuring the effects of feeding FAW-SPR leaf material from maize plants comprising event TC1507 (express Cry1F) on neonates (larvae <24 h after hatch). The test system targeted the use of neonates which were exposed to one leaf disc, of either the test or control substances, in a multi-arena tray. The leaf discs were the only food source for larvae for the duration of the experiment. Fresh leaf discs were added as needed to provide a constant source of food. Greenhouse collected leaves were rinsed with tap water. Multi-arena trays where controlled for humidity by placing a bottom-layer of agar into each well. This test system has already been validated and used for measuring insecticidal effects of plant-incorporated proteins.

Larval exposure to fresh leaf tissue was chosen as a means of administration because it is representative of insect exposure to plant-incorporated protectants in field conditions.

Moreover, the effects of these insecticidal proteins are both antibiotic and antixenotic, and exposure to plant tissue may be more ecologically realistic. This method of administration was chosen over a diet-based dose-response assay using pure protein or lyophilized plant tissue because of confounding effects that could result from trying to mimic field-relevant larval exposure.

The test substance was fresh, greenhouse-grown leaf tissue from hybrid maize plants containing event expressing the *Bacillus thuringiensis* Cry1F insecticidal protein (event TC1507). The control for natural effects of the test system (negative control) was fresh, greenhouse-grown leaf tissue from hybrid maize plants in similar genetic background (isoline maize) containing no events expressing insecticidal proteins (isoline maize). The control had one or both inbred parents in common with the test hybrid.

Tissue from both test and control substances were systematically sampled from similar leaves. Test and control substances were subjected to quantitative ELISA to determine level of Cry1F protein expression in TC1507 tissue and confirm absence of Cry1F protein expression in isoline tissue.

Trays were set up by preparing a 2% agar solution and pipetting 1 ml of warm agar solution into each well of a 128-well tray (CV International). The agar solution was allowed to cool and solidify and a disk of freshly collected corn leaf tissue was placed into each well. As tissue was collected for the experiment leaf punches were obtained for quantitative ELISA and submitted immediately for evaluation. One neonate FAW-SPR was placed in each well and a lid was placed securely to the top of the well to prevent insect escape. Insects were monitored daily for mortality and food reserves. Food was replaced as needed during the duration of the test. Neonate mortality was monitored daily, and mortality counts were taken at the end of the 4 day exposure period.

The trays were placed in a growth chamber with target temperature of 25° C. (±5° C.), relative humidity >60% and total darkness.

The experiment was conducted using a randomized incomplete block design with 32 replicates for test substance and 4 replicates for the control substance. Each replicate consisted of 16 observations per treatment in a multi-arena tray. The experimental unit was composed of an individual well in the 128-well tray (CV International). Each tray was labeled with the study number and individual treatments within each tray were labeled to identify treatment and the replication number using indelible ink. The treatment groups were as follows:

Treatment 1: 512 individuals of FAW-SPR fed leaf material from maize plants comprising the TC1507 event (Cry1F expressing event), and Treatment 2: 64 individuals of FAW-SPR fed leaf material from isoline maize plants that do not express Cry1F (negative control).

The results of FAW-SPR exposure to leaf material from maize plants expressing event TC1507 are presented in Table 2. No larvae from the susceptible strain (FAW-lab) were able to survive exposure to TC1507 leaf material (Table 2). Data presented shows that the FAW-SPR population was able to survive exposure to TC1507 plant material similarly to its survival on isoline maize plant tissue, suggesting a significantly decreased level of susceptibility to the Cry1F toxin.

TABLE 2

Response of FAW-SPR and FAW-lab to Feeding on Cry1F-Expressing Leaf Material from TC1507 Maize Plants

|         | Plant Material* | No. of Individuals | Mortality (%) |
|---------|-----------------|--------------------|---------------|
| FAW-SPR | TC1507          | 512                | 5.2           |
|         | Isoline         | 64                 | 4.7           |
| FAW-lab | TC1507          | 32                 | 100           |
|         | Isoline         | 32                 | 9.4           |

*TC1507 plant material comprises Cry1F. Isoline plant material lacks Cry1F.

Thus the present study indicated that the FAW-SPR field collected *S. frugiperda* population exhibited high levels of resistance to Cry1F as shown by the survival of neonates on TC1507 leaf tissue.

The development of a colony of fall armyworm which exhibit such a high degree of resistance presents several opportunities for investigation and use of colonies tolerant to the event. Additionally, because the resistance to the Cry1F was developed in the field, one would expect the FAW-SPR colony to more closely reflect tolerance which naturally develops through repeated field exposure rather than the artificial tolerance developed through progressive exposure in the lab.

EXAMPLE 3

Further Characterization of Cry1F Resistance in Fall Armyworm Using a Field-Derived Colony The Cry1F resistance that has been identified in fall armyworm (FAW) populations collected from Puerto Rico and used to produce the field-derived colony (FAW-SPR) that is described in Examples 1 and 2 was further characterized and used to estimate the risk of resistance evolution in populations of FAW that are currently susceptible to Cry1F.
1. Develop Genetic Stocks of Resistant FAW and Establish Bioassay Methods to Quantify Resistance Levels A key step in developing a rational resistance management strategy is to develop laboratory-selected colonies that exhibit high levels of resistance to a particular toxin.

The availability of resistant strains will allow subsequent genetic analysis of resistance inheritance, determination of the biochemical and physiological basis of resistance, and potentially, the development of molecular probes to monitor the evolution of resistance in the field. The resistant colony of FAW from Puerto Rico that is described in Example 1 above will be used as the starting material for the development of the laboratory-selected colonies.

Maintenance of the Cry1F resistant colony will be achieved by exposing neonate larvae to leaf material from maize plants expressing Cry1F. Individual neonate larvae (at least 1,000 per generation) will be exposed to leaf disks from maize hybrids comprising event TC1507. Surviving larvae (those that have initiated feeding and have grown beyond 1st instar) will be transferred to untreated diet and reared to adults using standard rearing techniques.

Bioassay of neonate FAW larvae was conducted to quantify the level of resistance identified in Cry1F resistant strain and to assess cross resistance to other Bt toxins. Bioassays involved techniques previously developed for assays with European corn borer (Marcon et al. 1999). Exposure to Bt toxins were applied to the surface of single wells of artificial diet is performed in 128 well trays (each well 16 mm diameter×16 mm height; CD International, Pitman, N.J.). Toxin solutions were prepared in 0.1% Triton-X 100 to obtain uniform spreading of Bt solution on the diet surface. Individual neonate larvae were placed in diet-containing wells, and mortality and combined larval weight were recorded seven days later. Control treatments consisted of wells treated with 0.1% Triton-X 100. When recording mortality, larvae that had not grown beyond first instar (i.e., <0.1 mg) were considered to be dead. Bioassays were conducted in duplicate on three different dates and included at least five Bt concentrations that produced mortality >0 but <100%. Data were analyzed by probit analysis (Finney (1971) "Probit analysis," Cambridge University Press, England; LeOra Software (1987) "POLO-PC. A user's guide to probit and logit analysis," Berkeley, Calif.) to determine lethal concentrations. Observed mortality is corrected for mortality in control treatments, and lethal concentrations with 95% fiducial limits are calculated. Larval weights are transformed to % growth inhibition relative to the controls, and these data are analyzed by non-linear regression (Marçon et al. (1999) *J. Econ. Entomol.* 92:2799-285). Bioassays of the selected colony will be compared with at least two unselected laboratory colonies currently available in our laboratory to estimate resistance ratios.

To measure survival of the selected colony on Cry1F expressing corn tissue, leaf discs from V3-V5 corn plants that have been maintained under greenhouse conditions and which have been tested for Cry1F expression using standard immunoassays will be utilized. Leaf discs (0.5 cm diameter) are placed on top a well of solidified agar in the bioassay trays described above, and a single neonate is placed in each well. Larvae are allowed to feed for four days, and mortality and qualitative estimates of leaf consumption are recorded after four days. Responses to both Cry1F expressing plants and non-Bt isoline plants will be determined for both the selected and control strains.

2. Determine the Inheritance of Resistance (i.e., Dominance, Sex-Linkage, Number of Resistance Genes)

One key component of successful resistance management of any pest species is determination of the genetic expression of resistance (i.e., dominant of recessive, autosomal vs. sex-linked) associated with a given resistance mechanism. Another important factor is to identify the number of genes associated with the resistance. Genetic data are essential to distinguishing between cross-resistance (the occurrence of one mechanism which confers resistance to several different toxins) and multiple resistance (several co-existing mechanisms, each of which confers resistance to one or more different pesticides). Additionally, some resistance management tactics, such as the high-dose/refuge approach proposed for Bt corn, are dependent on a given inheritance pattern although data to support such an inheritance are usually lacking. Finally, the availability of strains of known susceptible and resistant genotypes can be used to improve diagnostic bioassays used in monitoring programs.

The inheritance of Cry1F resistance was determined using reciprocal crosses of resistant and susceptible parents. A portion of the F1 progeny from individual crosses was bioassayed for Bt susceptibility using techniques previously described. The mortality curves were evaluated for sex-linkage and for assessing the degree of dominance (Stone (1968) Bull. WHO 38:325-329; Alves et al. (2006) *J. Econ. Entomol.* 99:494-501). Because resistance was due to an autosomal trait, progeny from single pair crosses were back-crossed to either the susceptible or resistant parental strain. The progeny were bioassayed to determine whether the resistance is conferred by a single genetic factor or if multiple genes were involved based on departure from the expected 1:1 ratio of RS to SS genotypes for a single factor inheritance. Response curves were generated for the various genotypes to estimate allele frequencies (see below).

3. Estimate Frequency of Resistance Alleles in Populations where Resistance has not Evolved Using Either an F1 or F2 Screen to Detect Resistance Alleles As described by Gould et al. ((1997) *PNAS* 94:3519-3523) if a homozygous resistant strain (RR) is available and resistance is recessive, estimates of resistance allele frequency can be obtained through single pair matings of field collected individuals with resistant individuals from the resistant laboratory colony. Because resistance alleles are most likely to be present in heterozygotes prior to a resistance episode or control failure (Roush and Daly (1990) "The role of population genetics in resistance research and management," In *Pesticide resistance in arthropods*, Roush and Tabashnik, eds., pp. 97-152, Chapman and Hall, NY), single-pair matings of the resistant lab colony (RR) with field collected individuals will result in progeny (F1) that are either 100% RS if the field collected individual is SS or a ratio of 1RR:1RS if the field collected parent carries one resistant allele. Screening these progeny at a concentration of Bt that discriminates between RS and RR genotypes would provide an efficient means of screening for rare resistance alleles. In the absence of a resistant strain, similar estimates of allele frequencies can be determined using an F2 approach (Andow and Alstad (1998) *J. Econ. Entomol.* 91:572-578) in which an inbreeding step allows expression of recessive alleles.

Field collections of FAW were obtained as larvae from corn fields. A non-Bt field was selected that is as far as possible from the nearest Bt field to minimize the possibility that local selection could result in a non-uniform distribution of resistance alleles across the landscape and therefore artificially raise the estimate of resistance allele frequency.

4. Consequences of Resistance on Reproductive Fitness

Trade-offs (negative associations between traits) commonly occur between key organismal traits such as fecundity, longevity, and duration of development and strongly constrain the evolution of individual traits. There is a growing appreciation of the importance in resistance management of identifying trade-offs between resistance and other traits, especially with regard to resistance mitigation. One focus of insect resistance management (IRM) research is to document the existence of trade-offs between resistance and fitness components for resistant strain. The existence of such trade-offs, or lack thereof, will influence the particular strategy used to manage resistance and potentially mitigate a resistance outbreak if it occurs.

Information on the potential trade-offs between resistance to Bt toxin and other organismal features will come from the mechanistic studies of Bt resistance in the resistant field population from Puerto Rico. Before we initiate fitness comparisons, we will establish near isogenic resistant and susceptible lines by repeated crossing and back-crossing combined with selection to minimize genetic differences between strains that might confound assessments of fitness trade-offs. Key fitness traits such as development time, fecundity, and longevity in susceptible and resistant strains will be measures. Pupae will be isolated individually from the resistant and susceptible strains to obtain virgin males and females. Emergent male-female pairs will be held in "honeymoon cages" so that fitness parameters (pupal weight, # egg masses, egg mass weight, time to first oviposition, and longevity) can be recorded for individual pairs (Siegfried et al. (2001) *Entomol. Exper. Appl.* 100: 15-20).

EXAMPLE 4

Level of Resistance in Fall Armyworms from FAW-SPR

To assess the level of resistance in fall armyworms from FAW-SPR, bioassays were conducted with FAW from the FAW-SPR colony disclosed in Example 1 and susceptible FAW from a laboratory colony. The FAW were exposed to diets comprising varying amounts of Cry1F as described in Example 3. The results of bioassays were used to determine that the susceptible colony had an $LC_{50}=18.6$ ng/cm$^2$, the resistant colony (FAW-SPR) had an $LC_{50}$ of greater than 7200 ng/cm$^2$. The diagnostic concentration was also determined to 200 ng/cm$^2$ and resistance ratio was greater than or equal to 387.1

EXAMPLE 5

Inheritance of Resistance in Fall Armyworms from FAW-SPR

To assess the inheritance of resistance in fall armyworms from FAW-SPR, reciprocal crosses between resistant FAW from the FAW-SPR colony disclosed in Example 1 and susceptible FAW were made, the resulting progeny assayed for mortality, and mortality curves prepared as described in Example 3. Backcrosses were also conducted as described in Example 3.

The results of the reciprocal crosses and backcrosses are illustrated in FIGS. 1 and 2, respectively. The results revealed that the inheritance of resistance in FAW-SPR is recessive, autosomal, and conferred by a single gene.

EXAMPLE 6

Frequency of Resistance in Fall Armyworm Populations in Texas and Florida

Fall Armyworms were collected from fields in Texas and Florida where FAW resistance to Cry1F has not evolved. There is limited interaction between FAW from Puerto Rico where resistance has evolved and FAW in Texas. However, there is known to be a significant exchange between FAW in Puerto Rico and Florida (Nagoshi et al. (2010) *J. Econ. Entomol.* 103:360-367). FAW from FAW-SPR were crossed with individuals from the Texas and Florida populations and the progeny bioassayed for mortality as described in Example 3. The results of the bioassays are summarized in Table 3.

TABLE 3

Frequency of Resistance in Texas and Florida Populations of FAW.

|  | Florida | Texas |
|---|---|---|
| Families Tested | 29 | 18 |
| #SS | 23 | 18 |
| #Sr | 6* | 0 |
| #rr | 0 | 0 |

*Confirmed to be Sr in $F_2$.

From these results, the frequency of the resistant allele (r) in the Florida population was estimated to be approximately 0.1. In Texas population, the resistance allele was not detected.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications, patent applications, and nucleotide and amino sequences referred to by GenBank Accession Numbers are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for producing a field-derived colony of fall armyworms (FAW) that comprises decreased susceptibility to maize plants producing Cry1F, the method comprising:
   (a) collecting FAW from an agricultural field comprising maize plants that express Cry1F;
   (b) allowing the FAW to feed on a diet comprising an effective concentration of Cry1F of 200 ng/cm$^2$ or greater, wherein the effective concentration is sufficient to kill greater than 50% of the susceptible FAW;
   (c) selecting the surviving FAW;
   (d) determining the zygosity of the surviving FAW; and
   (e) forming a colony of surviving FAW that are homozygous for the field-evolved resistance to Cry1F and has a resistance ratio greater than or equal to 387.

2. The method of claim 1, further comprising:
   (a) mating resistant FAW from the field-derived colony with FAW that are susceptible to Cry1F, whereby progeny are produced; and
   (b) analyzing the mortality rates of the progeny from each mating when grown in the presence of Cry1F.

3. The method of claim 2, further comprising backcrossing the progeny of (a) with resistant FAW from the field-derived colony.

4. The method of claim 2, wherein analyzing the mortality rates comprises preparing one or mortality curves.

5. The method of claim 2 wherein the method is used for determining the inheritance of resistance of in a field-derived colony of FAW that comprises field-evolved resistance to Cry1F.

6. The method of claim 1, wherein the diet comprises leaf material from maize plants comprising event TC1507.

* * * * *